United States Patent
Taylor

(10) Patent No.: US 7,212,932 B1
(45) Date of Patent: May 1, 2007

(54) **METHOD FOR EMULATING VISIBLE ELECTROMAGNETIC SPECTRUM EMISSIONS OF MEMBER SPECIES OF *ARTHROPODA: INSECTA: COLEOPTERA: LAMPYRIDAE***

(76) Inventor: Stephen John Taylor, 13009 Rincon Rd., Apple Valley, CA (US) 92308

( * ) Notice: Subject to any disclaimer, the term of this patent is extended or adjusted under 35 U.S.C. 154(b) by 0 days.

(21) Appl. No.: 11/161,250

(22) Filed: Jul. 27, 2005

Related U.S. Application Data

(60) Provisional application No. 60/521,972, filed on Jul. 29, 2004.

(51) Int. Cl.
*G01R 13/00* (2006.01)
(52) U.S. Cl. .................................................. 702/66
(58) Field of Classification Search ................ 702/66
See application file for complete search history.

(56) References Cited

U.S. PATENT DOCUMENTS

| | | | | | |
|---|---|---|---|---|---|
| 3,736,683 | A | * | 6/1973 | Paquette | 40/429 |
| 5,495,690 | A | * | 3/1996 | Hunt | 43/17.6 |
| 6,851,208 | B2 | | 2/2005 | Carter | |

FOREIGN PATENT DOCUMENTS

| | | | |
|---|---|---|---|
| JP | 2003297586 | * | 10/2003 |
| JP | 2003317024 | * | 11/2003 |

\* cited by examiner

*Primary Examiner*—John Barlow
*Assistant Examiner*—Demetrius Pretlow

(57) ABSTRACT

A method of accurately emulating the visible electromagnetic spectrum emissions of member species of Arthropoda: Insecta: Coleoptera: Lampyridae by convergence of a programmable software program, a data memory, a data processor, a clock frequency timer, and visible light emitting device or devices.

2 Claims, 1 Drawing Sheet

Figure 1:
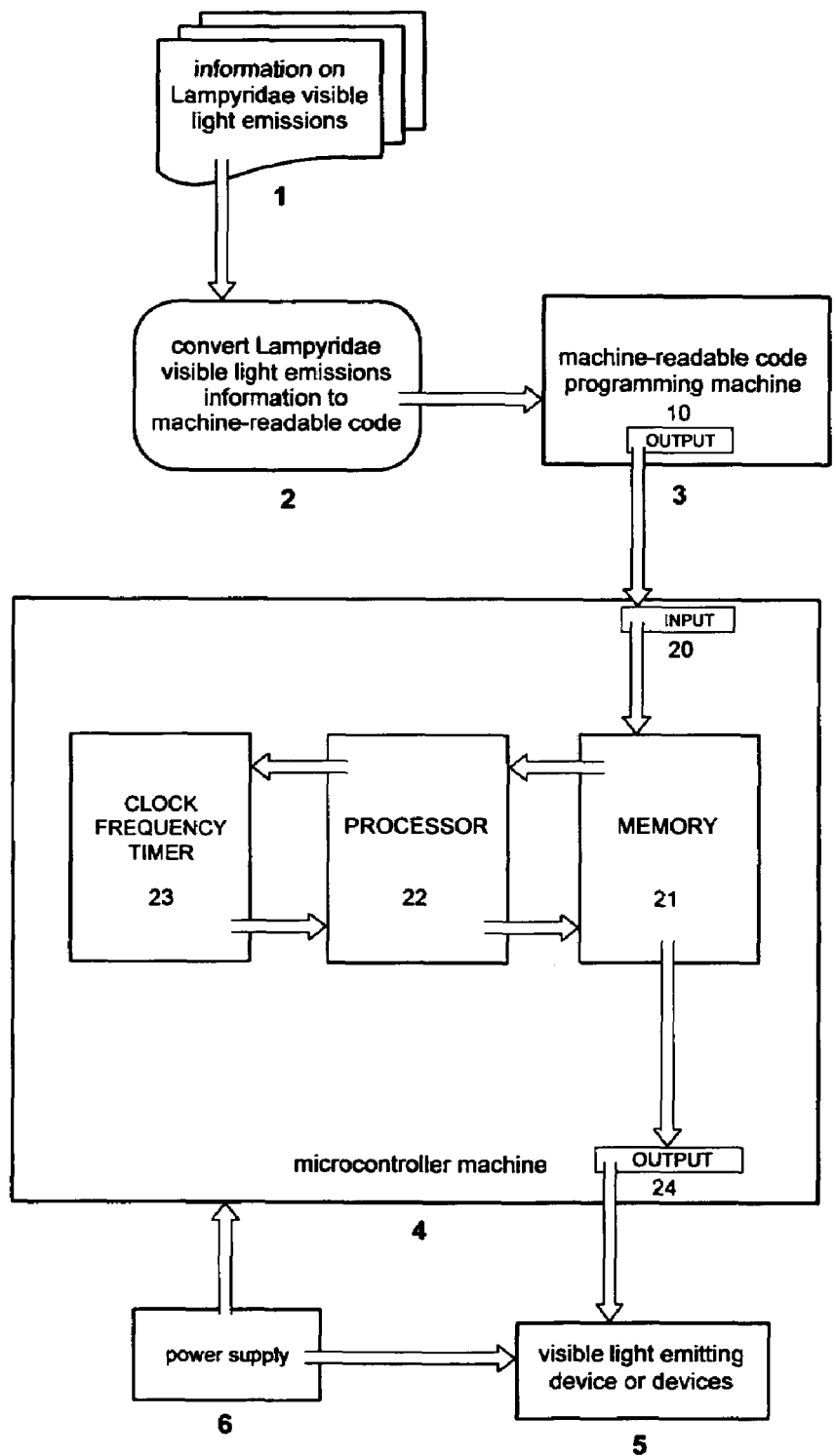

METHOD FOR EMULATING VISIBLE ELECTROMAGNETIC SPECTRUM EMISSIONS OF MEMBER SPECIES OF ARTHROPODA: INSECTA: COLEOPTERA: LAMPYRIDAE

BACKGROUND OF THE INVENTION

1. Field of Invention

This invention relates to accurately replicating, imitating, emulating, reproducing, and mimicking the visible electromagnetic spectrum light emissions of the bioluminescent abdominal 'lantern' of member species of the Lampyridae Family.

2. Prior Art

There are over 2000 species of Lampyridae in the world, each with their own unique flash pattern, bioluminescent lantern size and color. The desire for a methodology to accurately emulate this visible light output has increased due to the importance and value of Lampyridae research in recent years.

To accurately emulate the wide variety of Lampyridae emission permutations requires a methodology to accurately control a light emitting device or devices that are proximate in size and wavelength to the species and gender of Lampyridae being emulated. Further, variations in Lampyridae flash patterns are measured in milliseconds, and therefore an emulation device must have the ability to recreate those flash patterns with equal accuracy to be of scientific value.

The imitation of the visible electromagnetic spectrum light output of member species of the Lampyridae family of insects has been accomplished in the past by a variety of rudimentary means that lack scientific accuracy.

The most widely recognized means of imitating the visual lighting effect of Lampyridae is in the Pirates of the Caribbean attraction at the Disneyland theme park in Anaheim, Calif. It is the inventor's understanding that the visible light output of those artificial Lampyridae results from attaching an incandescent lamp approximately ⅛ inch in length onto one side of a circular disc of approximately 2 inches in diameter. The incandescent light and disc are suspended from thin wires thus permitting movement as a centrifugal blower on the floor below directs a continuous flow of air toward the hanging light with attached disc. As the airflow intersects the disc, movement of the disc and attached light ensues, including swinging and twisting motions, which when viewed from a distance appears as movement with an apparent on and off flashing of the light.

Rudimentary in design, the Disneyland artificial Lampyridae is not capable of producing accurate flash patterns of member species of Lampyridae and does not emit scientifically accurate wavelengths of visible light that match specific wavelength emissions of Lampyridae species. The use of suspended incandescent lamps, with attached discs and centrifugal blowers is acceptable for an environment where observers are controlled within defined viewing angles and distances, such as in the Pirates of the Caribbean attraction. However, this method of Lampyridae imitation is not satisfactory for less controlled environments. Additional disadvantages of this method of Lampyridae emulation include noise created by the centrifugal blowers, electric power required to operate the centrifugal blower(s) and the incandescent light(s), and the necessity to routinely replace the incandescent lights as their filaments fail. This methodology is not considered viable for scientific research or for generic creation of a Lampyridae environment.

A similar approach to Disney's imitation of Lampyridae visible light emission flashing is utilized by a Santa Barbara, Calif. company, Creativations, with a product called 'fireflies' that has a 'patent pending' mark on their literature. Their product utilizes a suspended horizontal wire from which vertical wires hang, each with a small electric fan in the middle of the wire and a light emitting diode (LED) at the end of the wire. The LED is covered with a black opaque substance eliminating light output from the device with the exception of a small area void of the opaque substance; thus creating a window that allows light emission. When electrical power is applied to the device, the LED and fan operate continuously. The hanging fan creates oscillations in the suspension wire, and the LED at the end of the wire begins to move in a random manner. As the LED moves, the observer perceives the LED to be flashing as the transparent window moves in and out of the observer's field of vision.

The Creativations artificial Lampyridae are not capable of accurately reproducing or replicating the controlled flash patterns of any member species of Lampyridae. The use of suspended LEDs with attached fans is acceptable for an environment where observers maintain some distance, as the fans and lights are in motion and the fan motors produce a high frequency sound. However, for scientific research this methodology is not viable.

Other devices used to mimic Lampyridae do not correspond scientifically to the visible light emissions of Lampyridae species. These devices utilize fixed and/or random timing devices that while creating a series of flashes, do not accurate emulate living Lampyridae species. Furthermore, they do not have the ability to be programmed to accurately emulate any one of the over 2000 species of Lampyridae in the world.

Although various methods, both mechanical and electrical, have been utilized in an attempt to mimic the visible light emissions of Lampyridae, none of these methods have scientifically recreated an accurate emulation of Lampyridae visible light emissions. Moreover, they specifically fail in their ability to accurately recreate, mimic, imitate, and emulate the flash rate timing, duration, delay, decay, and fade patterns unique to each Lampyridae species. Therefore, all Lampyridae visible light emission imitative methods heretofore have lacked both visual and scientific accuracy.

BACKGROUND OF INVENTION—OBJECTS AND ADVANTAGES

Accordingly, the several objects and advantages of the present invention are:

(a) to provide a method which accurately emulates, reproduces, mimics, imitates, replicates, and recreates the visible electromagnetic spectrum emissions of members of the Lampyridae species;

(b) to provide a method by manner and means to present to Lampyridae species members, and to human observers, a visible electromagnetic spectrum emission that is indiscernible from a living Lampyridae insect;

(c) to provide a method by which the unique visible flash emission timing and duration patterns for any Lampyridae species can be accurately recreated;

(d) to provide a method by which scientific researchers may recreate the visible light emission flash patterns of various species of Lampyridae to an accuracy level that will attract and lure living Lampyridae target species; and (e) to provide a method by which imitative visible light emissions may be produced which appear as living Lampyridae for observation in environments that may or may not be compatible, sustainable, or maintainable for living Lampyridae species.

Still further objects and advantages will become apparent from a consideration of the ensuing description and drawing.

SUMMARY

In accordance with the present invention a method for accurate emulation of all aspects of the visible electromagnet spectrum emissions for member species of Lampyridae.

BRIEF DESCRIPTION OF THE DRAWING-FIG. 1

1 represents the process of accumulation of information on Lampyridae visible light emissions, including frequencies, wavelengths, duration, repetitiveness, decay, intensity, size, and other information pertinent to accurately emulating Lampyridae emissions.

2 represents the process of converting information on Lampyridae visible light emissions into machine-readable code.

3 represents a machine-readable code programming machine capable of inputting machine-readable code into the memory of a microcontroller machine.

4 represents a microcontroller machine capable of receipt of data input, storage of data, processing of data, and output of data.

5 represents a plurality of light emitting devices.

6 represents a method of supplying power to the microcontroller machine and the visible light emitting device or devices.

DRAWING--REFERENCE NUMERALS

10 Data output port(s) of machine-readable code programming machine
20 Programming input port(s) of microcontroller
21 Memory sections of microcontroller
22 Data processing sections of microcontroller
23 Clock frequency timing sections of microcontroller
24 Data output port(s) for microcontroller

DETAILED DESCRIPTION

A preferred embodiment of the method of Lampyridae visible electromagnetic spectrum emission emulation for the present invention is illustrated in 1 through 6. Process initiation is at 1 as information is obtained on visible light emissions for a member species of Lampyridae. The desired information includes the flash rate frequency, flash duration, flash repetitiveness, flash decay, flash ramp, flash intensity, visible electromagnetic spectrum wavelength, lantern size, and other information pertinent to emulating the Lampyridae species and gender being emulated.

2 embodies the conversion of information collected in 1 into machine-readable code, known as a software program.

3 embodies a programming machine capable of transferring, or loading, machine-readable code software program through data output port 10 (3) into microcontroller data input port 20 (4).

4 embodies a microcontroller comprised of data input 20, memory 21, processor 22, clock frequency timer 23, and data output 24.

5 embodies one or a plurality of light emitting devices that emit visible electromagnetic spectrum emissions at the wavelength of the emulated Lampyridae species and gender, those wavelengths being between 690 nanometers to 450 nanometers. Further, that the size of emitting device or devices should be equivalent to the size of the emulated Lampyridae bioluminescent lantern, that being between 1 mm and 10 mm in diameter.

6 embodies a source of power in an amount to operate microcontroller 4 and visible light emitting devices 5.

OPERATION--FIG. 1

The manner of using this method to accurately emulate visible electromagnetic spectrum emissions of Lampyridae is comprised of a series of process steps beginning with investigation and information gathering in 1 to determine the specific emissions of a specific Lampyridae species and gender. A Lampyridae emits visible light from an abdominal segment, known as a lantern, using Nitrous Oxide induced bioluminescence for the purpose of locating a mate for procreation. The characteristics of the visible light emanating from the Lampyridae lantern varies by species and gender in wavelength, on and off duration, timing between on and off cycles, number of repetitive cycles, length of ramp during on cycles, length of decay during off cycles, intensity, and size of lantern. To accurately emulate a Lampyridae species, the methodology embodied in this invention reproduces each of the individualized and unique characteristics necessary for precise visual emulation, and has been scientifically validated by university research conducted in field studies with live Lampyridae.

The second process step 2 is the conversion of Lampyridae light emission research information into a machine-readable code, or a software program, that is subsequently input to a memory 21 of a microcontroller 4. The software input, or loading, is accomplished through a programming machine in 3. The machine-readable code can be of any software language that is operationally compatible with a processor 22. The processor must have an interface with a clock frequency timer 23 to allow accurate program timing sequences to be performed, including the ability to perform pulse width modulation functions that create fade transitions during ON and OFF phases often observed in Lampyridae light emissions.

After software program is loaded into memory 21 using input port 20, it shall remain static within memory. When power 6 is applied to microcontroller 4, processor 22 accesses memory 21 and clock frequency timer 23 to begin running loaded software program. Output port(s) 24, controlled by software program, turns output signal ON, OFF, or modulated. Output signal is sent to a light emitting device(s) 5 which respond by turning ON, OFF, or fade up (ramp) or down (decay). By accurate programming of software 2 flash pattern sequences for any species and gender of Lampyridae can be accurately emulated using the methodology of this invention.

The preferred embodiment of light emitting device(s) 5 is solid state light emitting diodes with wavelengths between 690 nanometers and 450 nanometers and physical size between 1 mm and 10 mm in diameter so as to match the bioluminescent abdominal lantern of the species and gender of Lampyridae being emulated. The number of light emitting devices 5 connected to a microcontroller 4 may be as few as one, or a plurality. The light emitting device or devices may be proximate to the microcontroller or may be non-proximate to the microcontroller with output 24 signals delivered through electrical wire connections. Other embodiments of the light emitting device(s) include incandescent, plasma, and fiber optic technologies.

A power supply 6 has several variations for use in diverse environments. These include direct current (DC) battery power for remote or temporary operation or locations, solar power for permanent low maintenance operation and locations, and transformer power for connection to alternating current (AC) power sources, including household power for permanent operation and locations. As embodied, the method of supplying power may be either direct current or alternating current.

Advantages

From the description above, a number of advantages of my method for emulating visible light emissions of the Lampyridae species become evident:

(a) The method of using of a microcontroller whereby a memory, processor, and clock frequency timer are incorporated to create the ability for programming ON, OFF, delays, fade decay, and fade ramp output signals.

(b) The method of using microcontroller output signals to control a light emitting device or devices that accurately emulate the light emissions of the Lampyridae abdominal lantern output.

(c) The method of using a light emitting device or devices which are the same physical size as the Lampyridae lantern of the species and gender being emulated.

(d) The method of using a light emitting device or devices which produce the same electromagnetic spectrum wavelength output as the Lampyridae lantern of the species and gender being emulated.

(e) The method of supplying alternate forms electric power to the microcontroller machine and light emitting device or devices, those methods being either alternating current or direct current.

CONCLUSIONS, RAMIFICATIONS, and SCOPE

Accordingly, the reader will see that with over 2000 species of Lampyridae in the world, each with their own unique flash pattern, lantern color and size, a methodology to accurately emulate emission permutations is desirable for conducting scientific research and recreating artificial Lampyridae environments for education. Because variations in Lampyridae flash patterns are measure in milliseconds, an emulation method must have the ability to recreate the flash patterns with equal accuracy in order to be indiscernible from the living insects by both Lampyridae and human observers.

In the practice of this invention it is now possible to accurately emulate the visible electromagnetic spectrum emissions of any Lampyridae species and gender to a scientific level heretofore not achieved. The successful use of this methodology in university field research study of Lampyridae has validated its usefulness. And, that no like method has been heretofore used for this purpose it is believed to demonstrate novelty and unobviousness.

Although the description above contains much specificity, this should not be construed as limiting the scope of the invention, but rather providing illustrations of some of the preferred embodiments of the invention. Thus, the scope of the invention should be determined by the appended claims and their legal equivalents, rather than by the examples given.

What is claimed is:

1. A method of emulating visible electromagnetic spectrum emissions for member species of Arthropoda: Insecta: Coleoptera: Lampyridae, comprising:
    (a) providing a memory that is able to store a series of machine-readable coded instructions,
    (b) providing machine-readable coded instructions which can be entered into said memory,
    (c) providing an input device to load said machine-readable coded instructions into said memory,
    (e) providing a processor to access said memory with functionality to retrieve data from memory, process data, and output data to memory,
    (d) providing a clock frequency timing circuit interfaced with said processor to supply a time-based frequency count to said processor,
    (g) providing a plurality of visible light emitting optical output devices that will:
        (1) interface and receive activation signals from said memory and processing unit, and
        (2) emit visible electromagnetic spectrum emissions between the wavelengths of 690 nanometers and 450 nanometers, whereby said method of visible electromagnetic spectrum emulation produces visible light emissions indiscernible from emissions of living Lampyridae to both human observers and members of the Lampyridae species.

2. A device for emulating visible electromagnetic spectrum emissions for member species of Arthropoda: Insecta: Coleoptera: Lampyridae, comprising:
    (a) a memory that is able to store a series of machine-readable coded instructions,
    (b) machine-readable coded instructions which can be entered into said memory,
    (c) an input device to load said machine-readable coded instructions into said memory,
    (e) a processor to access said memory with functionality to retrieve data from memory, process data, and output data to memory,
    (d) a clock frequency timing circuit interfaced with said processor to supply a time-based frequency count to said processor,
    (g) a plurality of visible light emitting optical output devices that will:
        (1) interface and receive activation signals from said memory and processing unit, and
        (2) emit visible electromagnetic spectrum emissions between the wavelengths of 690 nanometers and 450 nanometers, whereby said device produces visible electromagnetic spectrum emulation of visible light emissions indiscernible from emissions of living Lampyridae to both human observers and members of the Lampyridae species.

* * * * *